United States Patent
Tochterman et al.

(10) Patent No.: US 8,590,128 B2
(45) Date of Patent: Nov. 26, 2013

(54) SELECTIVELY COATING LUMINAL SURFACES OF STENTS

(75) Inventors: Andrew J. Tochterman, Palo Alto, CA (US); William J. Fox, San Carlos, CA (US); Nathan Harold, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 231 days.

(21) Appl. No.: 12/960,389

(22) Filed: Dec. 3, 2010

(65) Prior Publication Data
US 2011/0073036 A1   Mar. 31, 2011

Related U.S. Application Data

(62) Division of application No. 11/312,139, filed on Dec. 19, 2005, now Pat. No. 7,867,547.

(51) Int. Cl.
*B23P 19/04*   (2006.01)
(52) U.S. Cl.
USPC .................................. 29/238; 29/270; 29/239
(58) Field of Classification Search
USPC ................ 29/238, 239, 235, 243.5, 270, 278; 81/120, 121.1; 427/2.24, 2.1
See application file for complete search history.

(56) References Cited

U.S. PATENT DOCUMENTS

| | | | |
|---|---|---|---|
| 5,061,275 A | | 10/1991 | Wallstein et al. |
| 5,168,781 A | * | 12/1992 | Tenuta .................. 81/121.1 |
| 5,824,049 A | | 10/1998 | Ragheb et al. |
| 5,992,000 A | * | 11/1999 | Humphrey et al. ............ 29/516 |
| 6,096,070 A | | 8/2000 | Ragheb et al. |
| 6,447,835 B1 | * | 9/2002 | Wang et al. .................. 427/2.24 |
| 6,605,110 B2 | | 8/2003 | Harrison |
| 6,669,980 B2 | | 12/2003 | Hansen |
| 6,673,154 B1 | | 1/2004 | Pacetti et al. |
| 6,673,385 B1 | | 1/2004 | Ding et al. |
| 2002/0012741 A1 | | 1/2002 | Heinz et al. |
| 2003/0003221 A1 | | 1/2003 | Zhong et al. |
| 2003/0088307 A1 | | 5/2003 | Shulze et al. |
| 2003/0139800 A1 | | 7/2003 | Campbell |
| 2004/0059409 A1 | | 3/2004 | Stenzel |

(Continued)

OTHER PUBLICATIONS

Aoki et al., "Endothelial Progenitor Cell Capture by Stents Coated with Antibody Against CD34", J. of Am. College of Cardiology vol. 45, No. 10, pp. 1574-1579 (2005).

(Continued)

*Primary Examiner* — Lee D Wilson
(74) *Attorney, Agent, or Firm* — Squire Sanders (US) LLP

(57) ABSTRACT

With abluminal side of a stent masked, the luminal side of the stent is selectively coated with a substance, such as an anticoagulant, a platelet inhibitor and/or a pro-healing substance. The stent can be masked by inserting it into a rigid mandrel chamber or by compressing a masking sleeve onto the outer side of the stent. A spray nozzle inserted into the masked stent spray coats the substance onto the luminal side. The sprayed coating can be cured onto the stent such as by inserting an electrical-resistance heater bar into the stent.

16 Claims, 6 Drawing Sheets

(56) References Cited

U.S. PATENT DOCUMENTS

| | | |
|---|---|---|
| 2004/0071861 A1 | 4/2004 | Mandrusov et al. |
| 2005/0069630 A1 | 3/2005 | Fox et al. |
| 2005/0074544 A1 | 4/2005 | Pacetti et al. |
| 2005/0107531 A1 | 5/2005 | Claude |
| 2005/0109167 A1* | 5/2005 | Ainsworth .................... 81/121.1 |
| 2005/0186248 A1 | 8/2005 | Hossainy et al. |
| 2005/0192662 A1 | 9/2005 | Ward |
| 2009/0288522 A1* | 11/2009 | Tseng ........................ 81/121.1 |
| 2011/0073036 A1* | 3/2011 | Tochterman et al. ......... 118/301 |

OTHER PUBLICATIONS

George et al., "Number and Adhesive Properties of Circulating Endothelial Progenitor Cells in Patients with In-Stent Restenosis", Arterioscler. Thromb. Vasc. Biol., pp. 1-4 (2003).

* cited by examiner

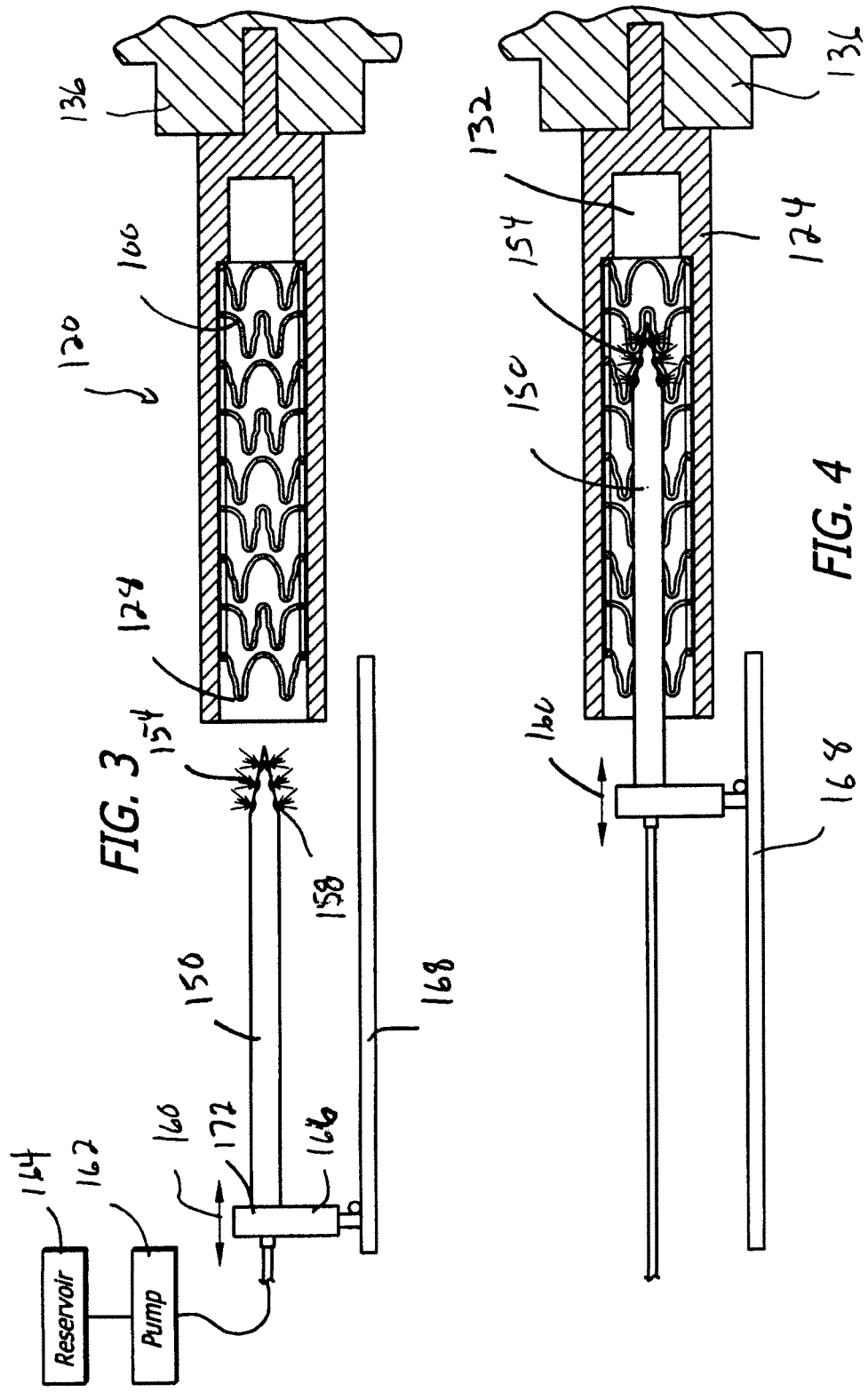

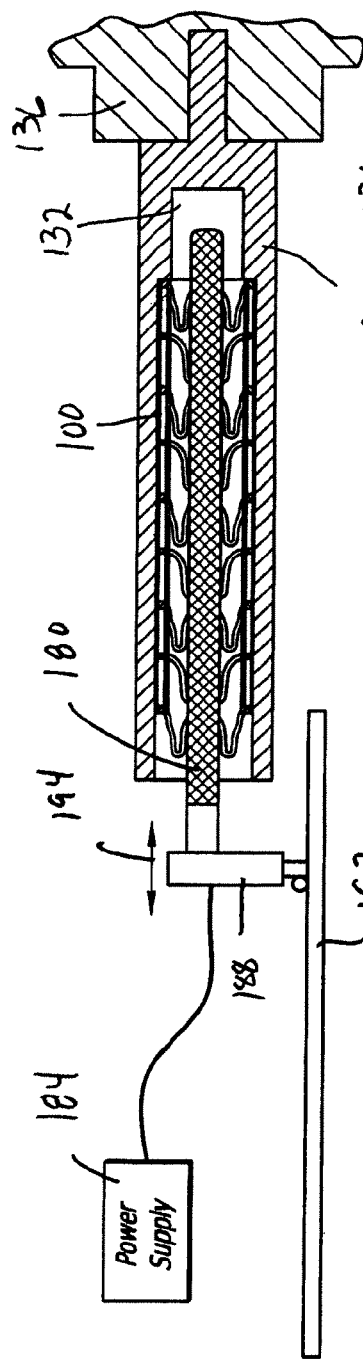
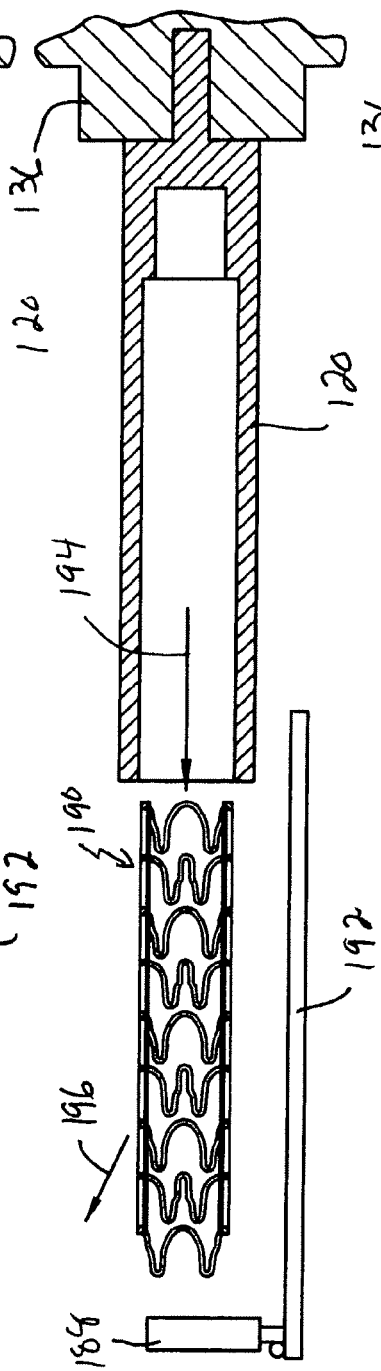
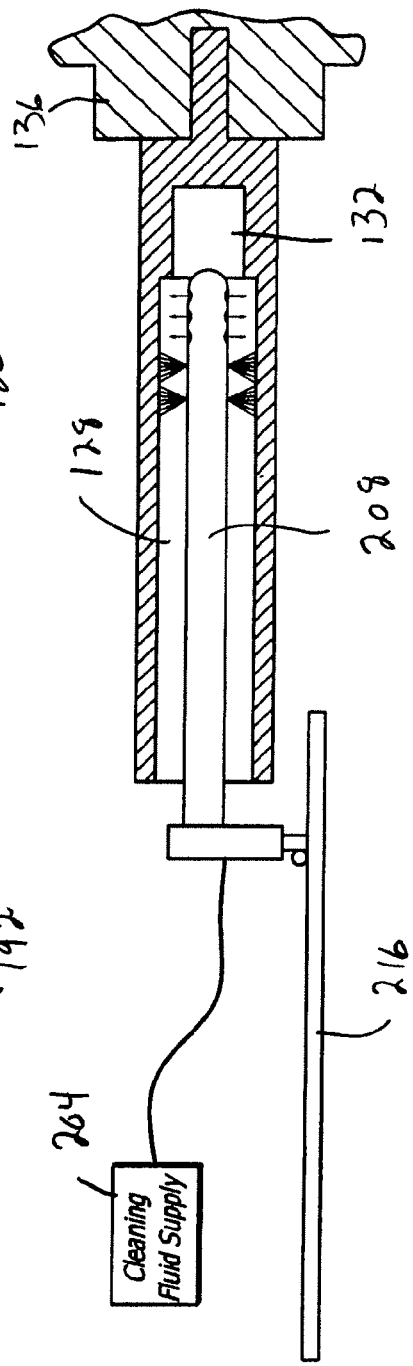

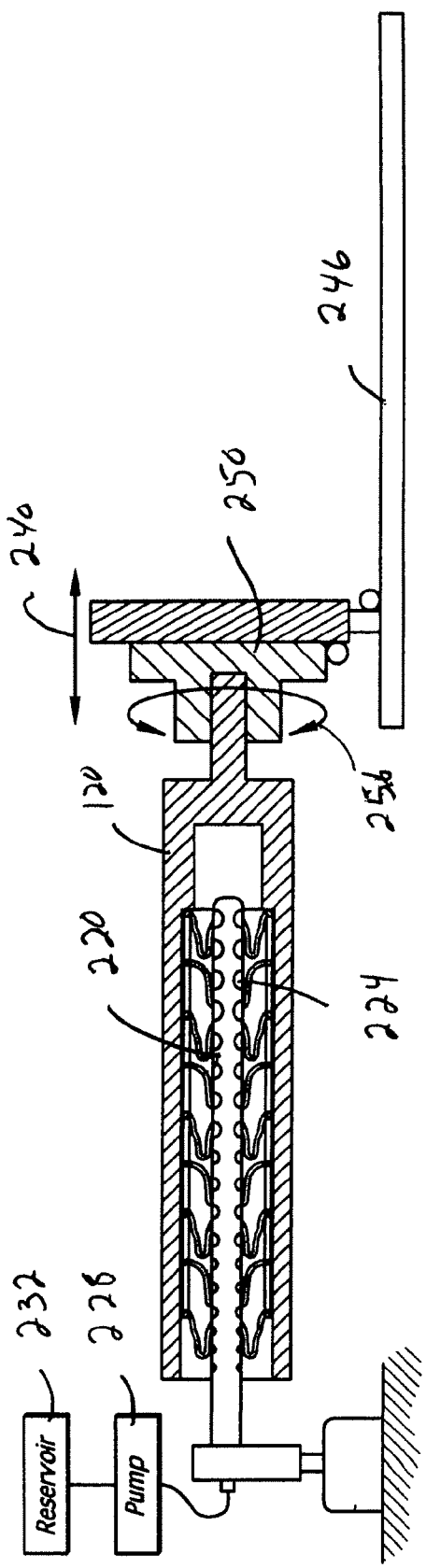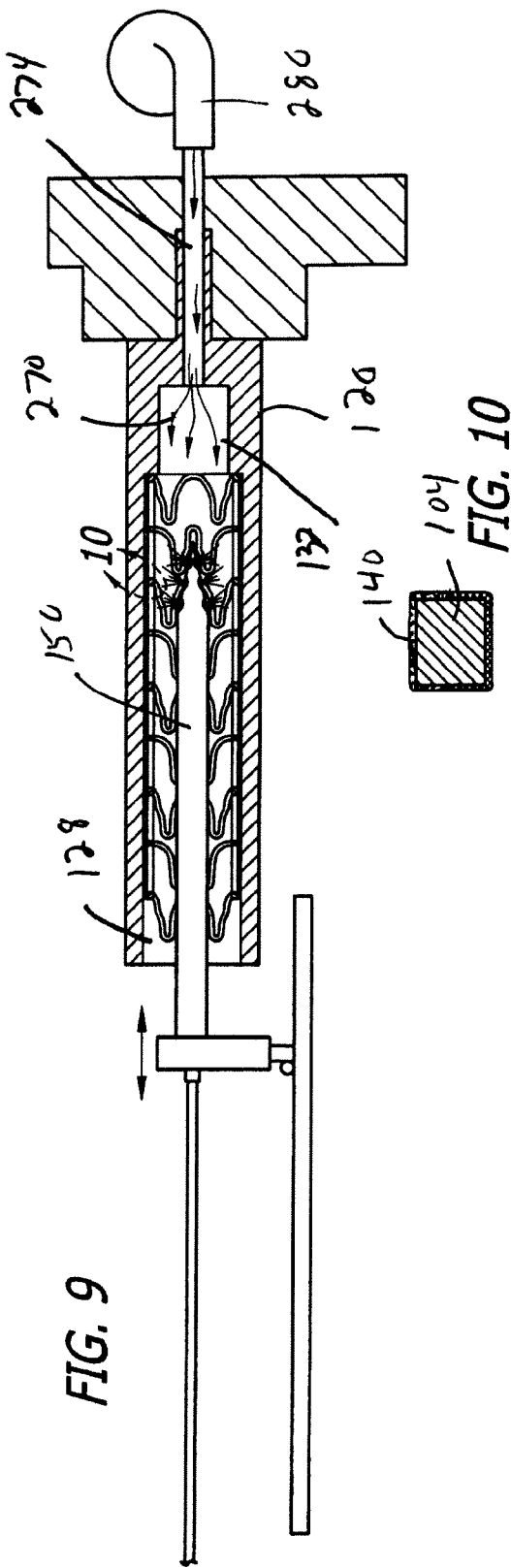

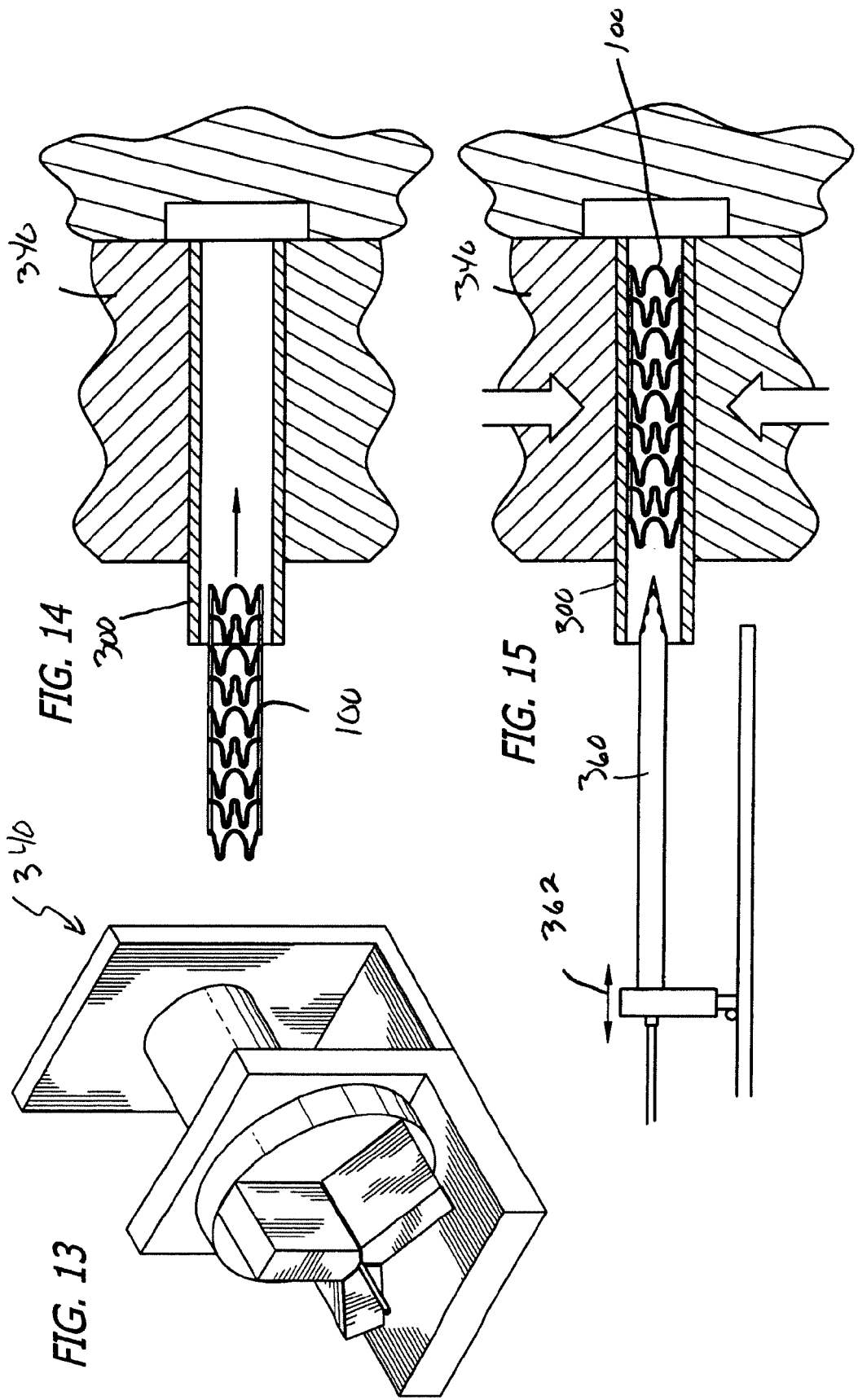

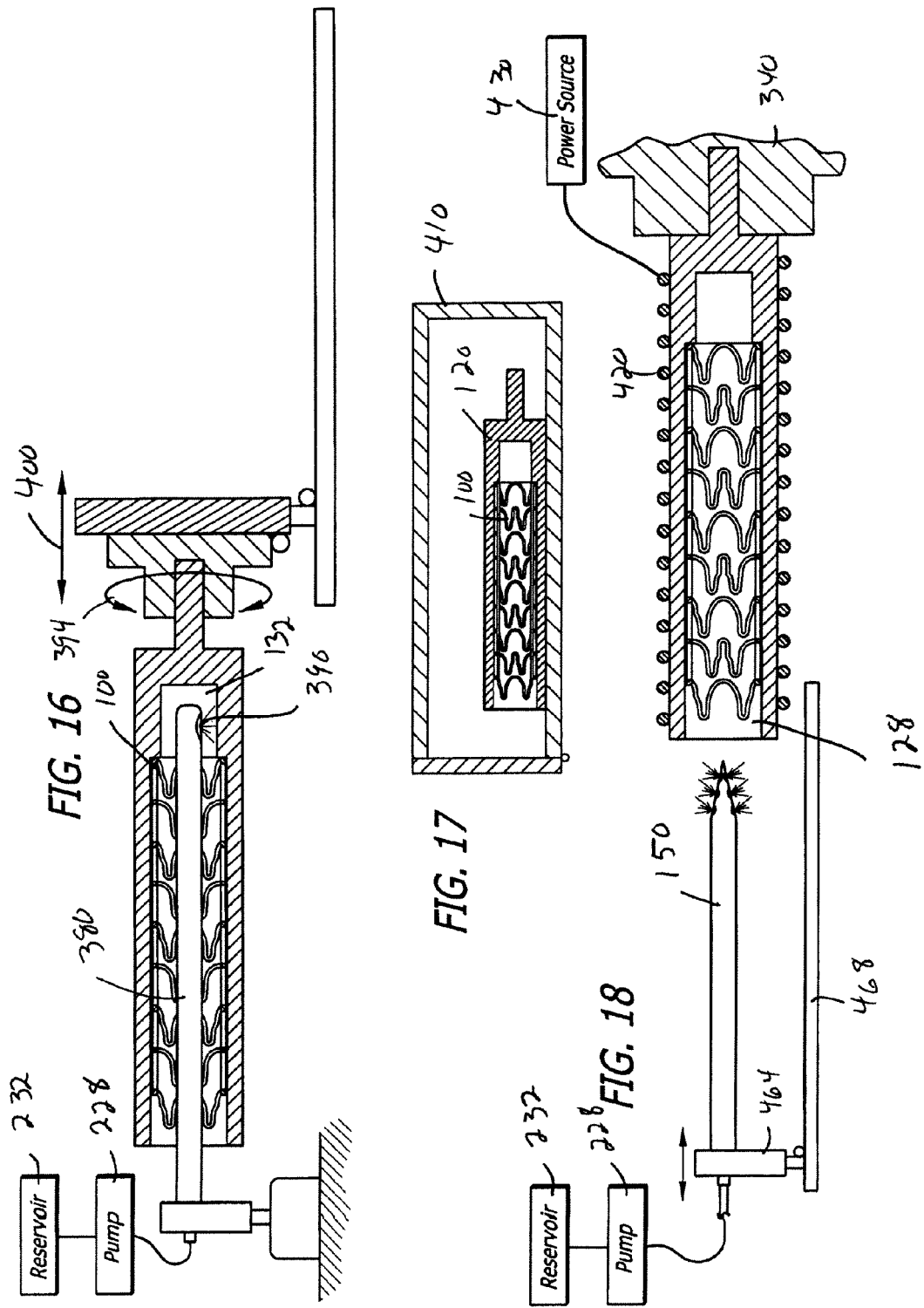

SELECTIVELY COATING LUMINAL SURFACES OF STENTS

CROSS REFERENCE

This is a divisional of application Ser. No. 11/312,139 filed Dec. 19, 2005, the contents of which is incorporated by reference in its entirety for all purposes.

BACKGROUND OF THE INVENTION

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to larger diameters once they are at the desired location. Examples of stents disclosed in the patent literature include U.S. Pat. No. 4,733,665 (Palmaz), U.S. Pat. No. 4,800,882 (Gianturco), U.S. Pat. No. 4,886,062 (Wiktor), U.S. Pat. No. 5,061,275 (Wallstein), and U.S. Pat. No. 6,605,110 (Harrison), and U.S. Pat. No. 2003/0139800 (Campbell).

FIG. 1 illustrates a conventional stent 100 formed from a plurality of struts 104. The struts 104 are radially expandable and interconnected by connecting elements or links 108 that are disposed between adjacent struts 104, leaving lateral openings or gaps 110 between adjacent struts 104. The struts 104 and the connecting elements 108 define a tubular stent body 112 having an outer, tissue-contacting abluminal surface and an inner, blood flow contacting luminal surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered than with systemic dosages that often produce adverse or even toxic side effects for the patient.

One method of medicating a stent uses a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer. Other known drug deposition methods include roll-coating, electrostatic spraying, and vapor deposition.

SUMMARY OF THE INVENTION

A shortcoming of the above-described methods of medicating stents is that both the inner surface and an outer surface of the stent are coated with the same therapeutic substance. Accordingly, the therapeutic substance will be dispensed locally by being absorbed by the vessel wall from the outer surface of the stent and will be dispensed downstream as blood carries the therapeutic substance from the inner surface of the stent. In some circumstances, there may be a need for coating the outer surface of the stent with a first type of a drug and the inner surface with a second type of a drug. For example, the stent's outer surface could be coated with an anti-inflamatory drug or anti-restenosis drug to treat inflammation or hyper-migration and proliferation of vascular smooth muscle cells, respectively. The stent's inner wall can be coated with an anti-coagulant (or platelet inhibitors or pro-healing agents pursuant to this invention) to reduce platelet aggregation, clotting and thrombus formation.

Thus, directed to remedying problems in the prior art, the present invention provides according to one embodiment thereof, a method which includes masking an abluminal surface of a stent, and coating luminal surfaces of the masked stent with a coating substance.

According to another embodiment of the invention, a coating method is provided which includes compressing a sleeve onto an abluminal surface of a stent to mask the abluminal surface, and coating a luminal surface of the masked stent with a coating substance. The substance can be a polymer-solvent-drug formulation. It can be a platelet inhibitor, an anti-coagulant and/or a pro-healing substance. The pro-healing substance can be a polymer or anti-body coating which facilitates the capture of the endothelial progenitor cells circulating in the bloodstream. The substance can also be an anti-proliferative substance and/or an anti-thrombotic agent or a bioactive coating. The substance coated on stent abluminal surfaces can be a polymer and an anti-proliferative drug coating, or can be a bio-absorbable polymer such as polyactide or polyethylene adipate.

According to a further embodiment of the invention, a coating method is provided which includes coating an abluminal surface of a stent or the entire stent with a first coating substance, and selectively coating a luminal surface of the stent with a second coating substance.

According to another embodiment of the invention, a coating method is provided which includes inserting a heating mechanism into a stent having a luminal coating and thereby curing the luminal coating on the stent.

According to a further embodiment of the invention, a coating method is provided which includes inserting a spray nozzle inside of a stent, and spraying out the spray nozzle a substance on a luminal surface of the stent. This method can include moving rotationally and/or translationally at least one of the spray nozzle and the stent relative to the other during the spraying. After the spraying, the coating can be cured/baked on the luminal surface.

According to a still further embodiment of the invention, a coating method is provided which includes inserting a stent into a chamber of a mandrel, and coating a luminal surface of the inserted stent with a coating substance. The coating can include positioning a spray nozzle into the inserted stent and spraying the coating substance out of the spray nozzle. The mandrel can include a pocket at an end of the chamber, and the positioning can include positioning a tip of the spray nozzle in the pocket. The method can further include after the spraying, inserting a heater mechanism into the inserted stent with a tip of the heater mechanism in the pocket and curing/baking the coating substance onto the luminal surface, or injecting hot gas into the stent to thereby curing/baking the coating substance onto the luminal surface.

According to another embodiment of the invention, a stent construction is provided which includes a stent and a first substance selectively coated on a luminal surface of the stent, and a different second substance coated on abluminal surfaces of the stent.

According to a further embodiment of the invention, a stent coating assembly is provided which includes a compressible sleeve, and compressing means for compressing the sleeve onto abluminal surfaces of a stent positioned therein to thereby mask the abluminal surfaces. The compressing means can be mechanical compressing means or pneumatic compressing means.

According to a still further embodiment of the invention, a stent coating system is provided which includes holding means for holding a stent, and coating means for selectively coating luminal surfaces of the stent, which is held by the holding means, with a coating substance.

According to another embodiment of the invention, a coating method is provided which includes curing/baking the luminal surface coating of a stent. The curing/baking can include positioning the mandrel and stent in an oven, heating the mandrel with a heating mechanism positioned in the stent, directing hot gas into the interior of the stent through an opening in the mandrel, or applying heat to the mandrel via a heating unit (such as a heater coil) on and encircling the mandrel.

According to another embodiment of the invention, a stent coating assembly is provided which includes a mandrel, wherein the mandrel includes chamber means for receiving therein a stent and for masking abluminal surfaces of the received stent such that luminal surfaces of the received stent can be selectively coated with a coating substance.

Other objects and advantages of the present invention will become more apparent to those persons having ordinary skill in the art to which the present invention pertains from the foregoing description taken in conjunction with the accompanying drawings.

BRIEF DESCRIPTION OF THE DRAWINGS

FIG. 3 is a side view similar to FIG. 2 with the stent in the mandrel, the mandrel secured in place, and a spray nozzle of the invention ready for insertion into the stent.

FIG. 4 is a view similar to FIG. 3 showing the nozzle in the stent and spray coating the luminal surfaces thereof.

FIG. 5 is a side view showing a heater bar of the invention in the stent after the spray coating of FIG. 4.

FIG. 6 is a view similar to FIG. 5, but after the drying step and showing the luminal surface coated stent being removed from the mandrel.

FIG. 7 is a side view showing the interior surface of the mandrel being cleaned after the luminal surface coated stent has been removed therefrom.

FIG. 8 shows an alternative to the spray coating embodiment of FIG. 4 wherein the nozzle is fixed and the stent is rotated and moved laterally relative thereto.

FIG. 9 is an alternative to the curing/drying embodiment of FIG. 5 wherein instead of a radiating heater bar, the curing/drying is accomplished by injecting hot gas into the opposite end of the mandrel, after the spraying operation.

FIG. 10 is an enlarged view of a portion of the stent taken on circle 10 of FIG. 9 and showing the different abluminal and luminal surface coatings on the stent.

FIG. 13 is a perspective view of a mechanical compressing mandrel or sleeve assembly, as an alternative to the pneumatic arrangement of FIG. 11, of the invention.

FIG. 14 is an enlarged side sectional view of a portion of the assembly of FIG. 13, showing a stent being inserted into position inside of the compressible sleeve of the assembly of FIG. 13.

FIG. 15 is a view similar to FIG. 14 showing the sleeve being mechanically compressed onto the sleeve, and a spray nozzle being inserted therein to spray coat the luminal surfaces of the stent whose abluminal surfaces have been masked by the compressed sleeve.

FIG. 16 is a view similar to FIG. 8, but showing an alternative spray nozzle construction and with the nozzle fully inserted into the mandrel.

FIG. 17 is a side view showing an alternative drying embodiment wherein the mandrel holding the stent is positioned in a drying oven after the luminal surfaces of the stent have been spray coated.

FIG. 18 is a side view showing an alternative to the drying embodiment of FIG. 5 wherein instead of a heater bar being inserted into the stent, a heater (coil) sleeve positioned around the (tubular) mandrel is energized to heat the mandrel and the coated stent therein.

DETAILED DESCRIPTION OF PREFERRED EMBODIMENTS OF THE INVENTION

The present invention, as discussed in detail below with reference to the drawings, includes methods and apparatuses for selectively coating inner surfaces of stents and other implantable medical devices. Pursuant to a basic aspect of the invention, an outer diameter masking mandrel or a compressible sleeve is positioned about the stent. An inside-out coating process directly coats the inside or luminal surfaces of the stent. The coating is then cured onto the luminal surfaces.

Figure 1:
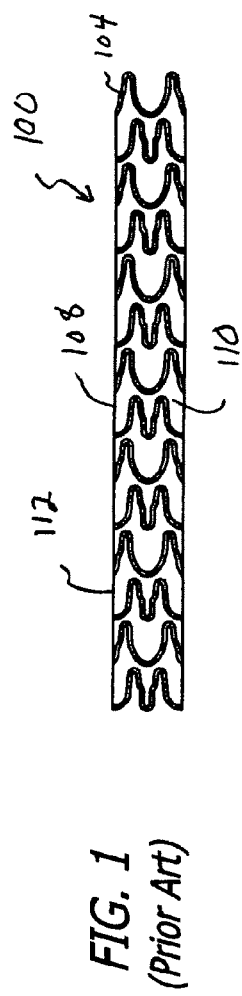
FIG. 1 is a side view of an exemplary stent as is known in the art.
Figure 2:
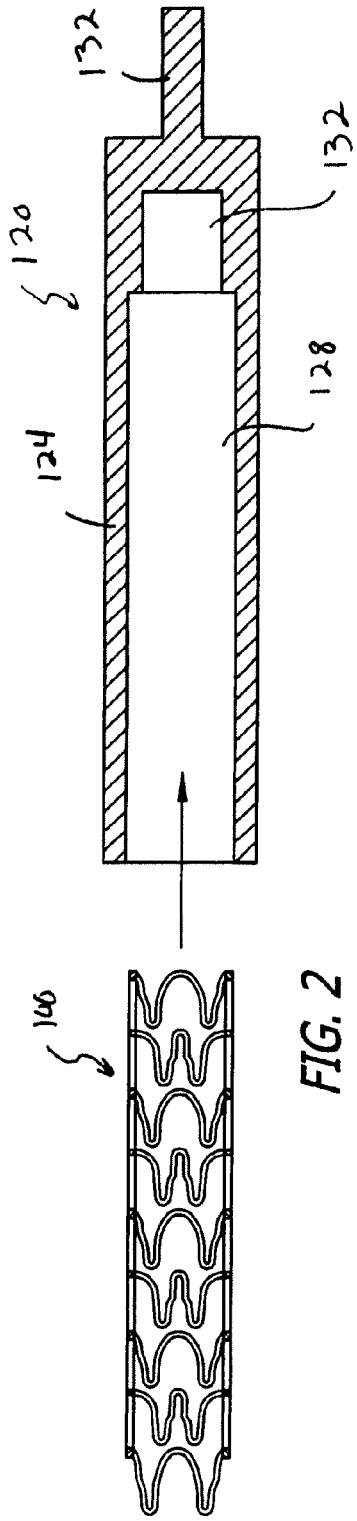
FIG. 2 is a side view showing the stent of FIG. 1 being inserted into a mandrel of one embodiment of the present invention.

Referring to FIG. 2, a mandrel of an embodiment of the present invention is shown generally at 120. The mandrel 120 has a fixed diameter sleeve 124 defining a rigid cylindrical chamber 128 dimensioned to receive a stent 100 therein. The chamber 128 can have a length equal to or greater than the length of a stent positioned therein. For example, the length can be approximately between ten mm and one hundred and fifty mm and a diameter of approximately between 1.14 mm and 11.00 mm. The mandrel 120 can be constructed of stainless steel, ceramic, glass, or other corrosion-resistant metal. A pocket 132 can be provided at the end of the chamber 128 for reasons which will become more apparent with respect to the descriptions of FIGS. 5 and 8 to follow. The pocket 132 has an opening smaller in diameter than that of the chamber 128. This smaller diameter provides for a rim or shoulder, as best illustrated in the figures, that stops the stent 100 from further penetrating into the chamber 128 or the pocket 132. A "nipple" 132 is provided at the end of the sleeve for fitting into a coating processor or other holding device 136, as shown in FIGS. 3 and 4.

The mandrel 120 is attached to the holding device 136, and the stent 100 is inserted into the mandrel chamber 128. Alternatively, the stent 100 can be inserted into the chamber 128 and then the mandrel 120 fixed into the holder 136. A further alternative is to have the mandrel 120 essentially permanently affixed to a holder. However, it may be advantageous to be able to remove it from the holder for cleaning purposes or for replacement, or for stent curing purposes, as discussed later.

The stent 100 when inserted into the mandrel chamber 128 can already have an abluminal or outer diameter coating 140 and/or can be completely coated. It can be a primered stent, that is, a stent coated with a primer adhesion layer. In other words, the stent 100 may be "drug" or "top coated," but need not be. Alternatively, the inner diameter can be coated first, as by methods disclosed herein, and then the outer diameter coated. (Examples of stent coating methods and coatings are disclosed in U.S. Pat. No. 6,673,154 (Pacetti et al.), U.S. 2003/003221 (Zhong et al.), U.S. 2003/0088307 (Shulze et al.), U.S. 2005/0186248 (Hassainy et al.), U.S. 2004/0071861 (Mandrusov et al.), 6,673,385 (Ding et al.), U.S. 2005/0192662 (Ward), U.S. 2005/0107531 (Claude) and U.S. 2005/010623 (Roorda et al.).) The outer diameter can be selectively coated, for example, by using an inner diameter masking mandrel, such as that disclosed in U.S. 2005/0069630 (Fox et al.)

Referring now to FIG. 3, with the stent 100 in position in the mandrel chamber 128 and the mandrel securely held in, preferably, a horizontal orientation, a spray nozzle 150 is inserted into the stent 100 and a coating 154 is sprayed onto the luminal surfaces of the stent 100. The spray nozzle 150 of FIG. 3 can have openings 158 three hundred and sixty degrees around the tip. The spray nozzle 150, inserted into the stent 100 as shown by the arrow 160 in FIG. 3, can be moved or oscillated back and forth laterally within the stent 100 to coat the stent surface as desired. A pump 162 to pump the coating substance from reservoir 164 can be used as well. The nozzle 150 can be moved by a powered trolley 166 running along a track 168. It should be noted that with any applicable embodiment disclosed herein, any one or a combination of the following movement can be used: rotation of the nozzle, linear movement of the nozzle, rotation of the stent, and linear movement of the stent.

The spray nozzle 150 can be a "pin" spray, smaller than the inner diameter of the stent 100, and made of stainless steel or other solvent-compatible material. This nozzle can have a hollow center providing the fluid path for the coating material. The tip of the nozzle 150 can be machined to permit a circular spray pattern, for example. The "pin sprayer" can be fitted inside a block 172 attached to the sprayer and attached at its backside to the fluid reservoir 164, similar to known syringe pump mechanisms.

The coating substance 154 can include a platelet inhibitor (such as Dipyridamole, Ticlopidine, Abciximab or Clopidigrel), an anti-coagulant (such as heparin, low molecular weight heparin or warfarin) and/or an agent used to capture endothelial progenitor cells (such as polysaccharide, collagen or fullerenes). See, George et al., "Number and Adhesive Properties of Circulating Endothelial Progenitor Cells in Patients with In-Stent Restenosis", Arteriosclerosis, Thrombosis, and Vascular Biology, 2003; 23; e57. See also Aoki et al., "Endothelial Progenitor Cell Capture by Stents Coated With Antibody Against (D34: the Healing-FIM (Healthy Endothelial Accelerated Lining Inhibits Neointimal Growth-First In Man) Registry," J. Am. Coll. Cardiol. 2005 May 17; 45(10): 1574-9. Additional inner diameter coatings include therapies such as anti-thrombotic agents, for reduction of fibrinogen and other thrombotic factors, and vasodilators, for increased diameter post-stent implantation. The coating applied to the luminal surface of the stent 100 can have a thickness of two to ten microns or more narrowly, four to six microns. The coating substance can include a polymer for include a drug free from any polymers. In some embodiments, the coating substance can be a bio-adhesive for improving stent retention of a catheter balloon.

After the coating step, the coating can be cured or baked onto the inner diameter of the stent 100. One method of doing this pursuant to the present invention is to insert a cylindrical electrical resistance heater bar 180 into the stent 100. This is shown in FIG. 5, where the heater bar 180 is powered by a power supply 184 and a powered trolley 188, traveling on a track 192, moves the bar controllably back and forth as indicated by arrow 194 in the stent 100 to dry the coating. The curing can be for between one and three minutes and at a temperature of approximately forty-five degrees Centigrade. The heating coil or bar 180 can be adjusted to a specific temperature to deliver a prescribed amount of heat to cure the coating before the stent 100 is removed from the mandrel. In other words, a cylindrical heat nozzle element with programmable temperature capabilities can be used to provide the heat needed to cure the inner diameter coating. There can be a drying period at ambient between the coating steps. After the luminal coating and before the final curing, the coating can be dried at ambient temperatures for approximately at least ten to fifteen seconds. In some embodiments, the length of the bar 180 can be the same or longer than the length of the stent 100 so as to provide for an even distribution of heat across the length of the stent 100. Referring to FIG. 5, the tip of the heater bar 180 when fully inserted into the stent can extend into the pocket 132 to thereby ensure that the substance on the distal end of the stent is fully and evenly cured.

Additional coating and curing steps may be conducted on the stent 100 as desired to coat the stent with the same substance or to coat it with different substances at different steps, as would be within the skill of those in this art from this disclosure. The entire stent surface can be first coated with a polymer and an anti-proliferative drug such as everolimus. Afterwards, an anti-coagulant or anti-thrombotic polymer coating can be applied to the stent inner diameter, and optionally sidewall surfaces, for example, by using the above-discussed mandrel or the below-discussed compressible sleeve. These successive steps may need inter-pass drying (or drying between coating steps). There may or may not be an oven bake or other curing process between application of the two different formulations, and this can depend on desired release kinetics and solvents used. In other words, a two-phase coating process can be used, namely: (1) with an anti-proliferative, and (2) with an anti-thrombotic agent or a natural biocoating (one that adheres endothelial progenitor cells for strut re-endothelialization). The order of coating can be either (1) then (2), or (2) then (1). It is also within the scope of the invention to blanket the stent 100 with a polymer "topcoat" to slow, retard or encapsulate the dual-therapies.

Most coatings need a final (oven) baking/curing process to drive off the remaining solvent. Temperature and time conditions are based on the solvent that is to be removed. The goal is to reduce residual solvent to a safe, non-toxic, perhaps non-detectable level, which reduces the risk of an adverse reaction by the body to the solvent. Ambient drying can be used, but it depends on the solvent. More particularly, existing formulations require oven baking or other curing to remove excess solvents. Any solvent which evaporates at room temperature might be too volatile to effectively spray coat as the solvent might evaporate before the spray droplets contact the stent surface. In addition, some initial residual solvent is desirable to allow the coating to create a uniform surface on the stent before drying.

The final drug baking can be at fifty degrees Centigrade for sixty to seventy-five minutes. This time/temperature would vary based on any adverse reaction or damage to the drug, the type of solvent being forcibly evaporated from the stent, and the desired release kinetics of the drug. Drying or solvent removal from the coating may have a significant impact on drug release kinetics upon implantation of the stent in the body of the patient.

After the coating and curing have been completed, the selectively coated stent 190 is removed from the mandrel 120 as shown by the arrows 194, 196 in FIG. 6, for any further manufacturing steps as may be needed.

The inside of the mandrel chamber 128 can then be cleaned. Referring to FIG. 7, this can be by using a cleaning fluid 200 from a supply 204 and sprayed out of a spray nozzle 208, which is mechanically driven back and forth on a track 216, to clean the inner circumference of the chamber 128. The chamber 128 can then be air dried and/or dried with a drying implement, as needed. This cleaning step may be done after each stent 100 is coated or as otherwise needed.

An alternative method of coating the luminal surfaces of the stent 100 is to have the spray nozzle 220 fixed and to move the mandrel 120 and thereby the stent 100 relative to the spray nozzle 220, as illustrated in FIG. 8. The spray nozzle 220 can have nozzle openings 224 along its entire length. The ones at the distal end can be slightly larger than ones at the proximal end as shown (in an exaggerated manner) in FIG. 8 to take into account spray fluid pressure drops. The coating material can be pumped by a pump 228 from a reservoir 232 and out through the openings 224 in the nozzle 220, as the mandrel 120 and thereby the stent 100 therein is moved translationally relative thereto as shown by arrow 240. This movement can be by a motorized movement along a track 246. If the nozzle openings extend a full three hundred sixty degrees around the nozzle, it may not be necessary to rotate the stent 100 around the nozzle 220. However, if they are not completely around the nozzle or as an alternative process, the stent can be rotated by the motor mechanism 250 as indicated by the circular arrow 256 in FIG. 8. Rotation of the stent 100 may provide for a more uniform application of the coating substance.

While an electrical resistance heater bar 180 for curing the coating material is illustrated in FIG. 5, an alternative is to use heated gas 270 (such as air) as shown in FIG. 9. This can, for example, be a "dry gas" or an inert gas so that curing/baking occur simultaneously. Referring to this drawing figure, the mandrel 120 can have a channel 274 at its end opposite to the stent insert end and communicating with the pocket 132 and thereby the chamber 128. A pump shown schematically at 280 can pump hot gas 270 into the interior of the stent 100 as shown by the arrows in FIG. 9. This can be done as the spray nozzle 150 is being removed as illustrated in FIG. 9 or after the spray nozzle 150 has been removed and ambient drying has occurred for a time. In some embodiment, one skilled in the art may appreciate that application of the gas may be suitable if conducted simultaneously with the coating deposition process. FIG. 10 illustrates an enlarged view of a strut 104 of the stent after a coating operation and showing the coating.

Figure 12:
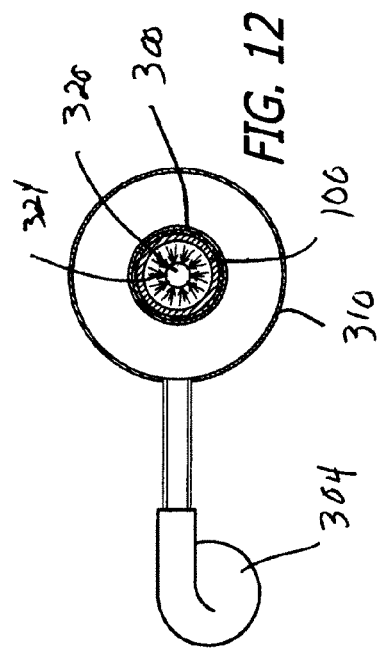
FIG. 12 shows the sleeve of FIG. 11 in position and the interior of the stent being spray coated.
Figure 11:
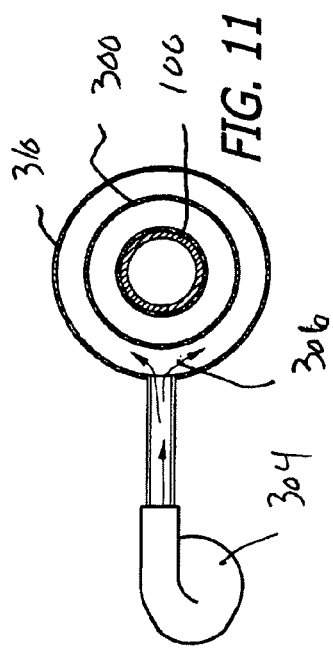
FIG. 11 shows an end view of an alternative mandrel arrangement where instead of a rigid mandrel sleeve as shown in FIG. 2, the "mandrel" is a compressible sleeve mask which is compressed with blown gas (pneumatically) onto the outside surface of the stent.

The mandrel 120 provides a fixed, rigid receiving chamber 128 for the stent 100. An alternative is to provide a compressible member and means for compressing the member onto the outside surface of the stent 100. This alternative arrangement does not require the tight exact tolerances of the rigid mandrel and also can compress tightly onto the abluminal surfaces of the struts of the stent and a very slight dimension into the cells or openings between struts. The compressible member can be a compliant sleeve 300 such as shown in end view in FIG. 11. The sleeve 300 can have a wall thickness of 0.005-0.010 inch, and can be made of a low Durometer (40-70 D) Pebax, Tecoflex or similar elastomer. A means for compressing this sleeve 300 is illustrated schematically as a pneumatic means where a pump 304 is provided to pump air 306 or other gas into a chamber 310 around the sleeve 300 and thereby compress the sleeve 300 onto the stent 100. The sleeve 300 is held on the stent 100 with the pneumatic pressure while the spray nozzle is inserted into the held stent 100 and the coating material sprayed thereon. The spray nozzle is shown in FIG. 12 at 320 and the coating material being sprayed is shown at 324 emanating therefrom. The pneumatically compressed sleeve 300 can also hold the stent while the sprayed substance is cured onto the luminal surfaces. This can be by a heater bar inserted therein, such as shown in FIG. 5, or by hot air injected through it similar to the method shown in FIG. 10.

Instead of pneumatically compressing the sleeve 300 onto the outer surface of the stent 100, the sleeve 300 can be mechanically compressed, as can be understood from FIGS. 13-15. Referring to FIG. 13, a mechanical radial-type crimper as shown generally at 340 can be used, and shown in enlarged partial cross section in FIGS. 14 and 15. In FIG. 14 it is shown in a normal or relaxed state with the sleeve 300 held therein and the stent 100 being inserted or positioned into the sleeve 300. FIG. 15 then shows with large arrows the sleeve 300 being compressed (for example by moving jaws of crimper 340 radially by electrical, pneumatic or hydraulic means) onto and around the stent 100 in a masked arrangement.

In this masked arrangement, with the abluminal surfaces of the stent 100 covered with the sleeve 300, the spray nozzle 360 can be inserted into the stent and the luminal surfaces sprayed with the coating material. This can be with a translational movement of the nozzle along the length of the stent (as depicted by arrow 362), and/or the stent 100 can be rotated and/or moved translationally relative to the nozzle as shown for the alternative embodiments for the mandrel arrangement. Additionally, a pocket similar to the mandrel pocket 132 can be provided in the mechanical or pneumatic sleeve compression arrangements.

FIG. 16 illustrates an alternative mandrel arrangement (or compressible sleeve arrangement) where the nozzle 380 does not have openings around its entire circumference, but rather only has openings around a partial part of the circumference such as a single opening 390 on a bottom surface thereof. To spray coat the entire circumference of the inner diameter of the stent 100, the stent 100 can then be rotated about the longitudinal axis of the nozzle 380 as indicated by the circular arrow 394 in FIG. 16. Further, the stent 100 can be moved translationally relative to the length of the nozzle 380, as shown by the arrow 400. FIG. 16 illustrates how the tip of the nozzle 380 can extend into the pocket 132 to thereby ensure that the most distal end portions of the stent 100 are completely coated.

An alternative means of curing the coating onto the inner diameter of the stent 100 is illustrated generally in FIG. 17 where the stent 100 conveniently held still in the mandrel 120 is positioned in a conventional baking oven 410. It is kept therein at the desired temperature and for the time needed for curing.

A further alternative means for curing the coating onto the inner diameter of the stent 100 is to use a heater sleeve. This sleeve is shown in FIG. 18 by a heater coil 420 powered by the power source 430 and wrapped around the outer diameter of the sleeve of the mandrel. When the coil 420 is energized, heat is transmitted through the mandrel into the chamber 128 to thereby cure the coating onto the inner diameter of the stent 100. Also illustrated in FIG. 18 is the spray nozzle 150 after a spraying operation and after having been removed from the stent 100. The pump and reservoir are shown schematically in this figure at 232 and 228, respectively, as is the trolley 464 for moving the stent 100 along the track 468.

Instead of spray coating the luminal surfaces they may be roll coated, dip coated, vapor deposition coated or electrostatic coated, as would be apparent to those skilled in the art from the present disclosure. Examples of electrostatic coating techniques are disclosed in U.S. Pat. Nos. 5,824,049 (Ragheb et al.), 6,096,070 (Ragheb et al.) and 6,669,980 (Hansen).

In summary, existing drug eluting or delivery stent therapies effectively provide localized therapies to the vessel wall where injury occurs upon stent placement. Stents of the present invention are coated with a therapy specific to the luminal surface and thereby effectively deliver local treatments into the bloodstream. Therapies which can be delivered by the inner diameter coatings are platelet inhibitors, anti-coagulants and pro-healing substances. Additional inner diameter coating therapies include anti-thrombotic agents and vasodilators.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. However, it is intended that all such variations not departing from the spirit of the invention be considered as within the scope thereof.

What is claimed is:

1. A support assembly, comprising:
a stent disposed within a chamber capable of masking an abluminal side of the stent, he chamber including:
an opening at a proximal end for inserting the stent into, and removing the stent from the chamber,
a shoulder disposed distally of the stent and having an inner diameter less than a diameter of the stent, and
a pocket disposed distally of the shoulder;
wherein the stent comprises a plurality of interconnected struts.

2. The support assembly of claim 1, further including a drive mechanism configured for advancing a spray nozzle or heating element into the chamber while the stent occupies the chamber.

3. The support assembly of claim 2, wherein the spray nozzle is a pin spray.

4. The support assembly of claim 2, wherein the spray nozzle is configured for producing a circular spray pattern.

5. A support assembly, comprising:
a stent disposed within a chamber capable of masking an abluminal side of the stent, the chamber including:
an opening at a proximal end for inserting the stent into, and removing the stent from he chamber,
a shoulder disposed distally of the stem and having an inner diameter less than a diameter of the stent, and
a pocket disposed distally of the shoulder; and
a nipple disposed distally of the pocket for placing a fluid source in fluid communication with the chamber.

6. The support assembly of claim 5, wherein the fluid source is heated air for drying the stent after applying a coating.

7. The support assembly of claim 1, wherein the chamber comprises a compressible member disposed about the stent.

8. A stent coating assembly, comprising:
a support including a chamber for receiving a stent; and
a pocket positioned at an end of the chamber such that an opening diameter of the pocket is smaller than a diameter of the chamber so as to prevent the stent from penetrating into the pocket; and
a coating applicator configured to be inserted into the chamber for coating the stent.

9. The assembly of claim 8 wherein the support is configured to mask an abluminal side of the stent during application of a coating composition to a luminal side to the stent.

10. The assembly of claim 8 wherein the length of the chamber is equal to or larger than the length of the stent.

11. The assembly of claim 8 wherein the support includes a channel or allowing gas to be applied into the chamber.

12. The assembly of claim 8 additionally comprising a heating element circumscribing at least a part of the support for providing heat into the chamber.

13. The assembly of claim 8 wherein the coating applicator can be moved back and forth with respect to the stent.

14. The assembly of claim 8 wherein the coating applicator can be rotated with respect to the stent.

15. A means for rotating the stent and moving the stent in a linear direction in combination with the assembly of claim 8.

16. The assembly of claim 8, further including a nipple disposed distally of the pocket for placing a fluid source in fluid communication with the chamber.

* * * * *